United States Patent
Pa (10) Patent No.: US 9,751,085 B2
(45) Date of Patent: Sep. 5, 2017

(54) SINGLE-PIECE FERRULE WITH UNDERCUT TAPERING PART

(75) Inventor: Ponna Peter Pa, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/412,654

(22) PCT Filed: Jul. 5, 2012

(86) PCT No.: PCT/US2012/045524
§ 371 (c)(1),
(2), (4) Date: Jan. 2, 2015

(87) PCT Pub. No.: WO2014/007820
PCT Pub. Date: Jan. 9, 2014

(65) Prior Publication Data
US 2015/0145246 A1    May 28, 2015

(51) Int. Cl.
*B01L 3/00* (2006.01)
*G01N 30/60* (2006.01)

(52) U.S. Cl.
CPC ............. *B01L 3/5635* (2013.01); *B01L 3/563* (2013.01); *B01L 3/565* (2013.01); *G01N 30/6026* (2013.01); *G01N 30/6039* (2013.01); *B01L 2300/0838* (2013.01); *Y10T 29/49* (2015.01); *Y10T 29/49826* (2015.01)

(58) Field of Classification Search
CPC ........ B01L 3/5635; B01L 3/563; B01L 3/565; B01L 2300/0838; G01N 30/6026; G01N 30/6039
See application file for complete search history.

(56) References Cited

U.S. PATENT DOCUMENTS

| D200,895 S | 4/1965 | Symonds | |
|---|---|---|---|
| 3,893,716 A | * 7/1975 | Moreiras | F16L 19/103 285/3 |
| 4,205,417 A | * 6/1980 | Mackal | A61M 25/1018 24/115 M |
| 4,304,422 A | * 12/1981 | Schwarz | F16L 19/103 285/341 |
| 4,586,731 A | * 5/1986 | Castrup | F16L 19/10 285/341 |

(Continued)

FOREIGN PATENT DOCUMENTS

| AU | WO 0173338 A1 * 10/2001 | ......... G01N 30/6026 |
|---|---|---|
| CN | 101124027 A | 2/2008 |

(Continued)

OTHER PUBLICATIONS

International Preliminary Report on Patentability for parent application PCT/US2012/045524 dated Jan. 6, 2015 (7 pages).*

(Continued)

*Primary Examiner* — Rodney Mintz (57) ABSTRACT

A single-piece ferrule for a fitting for coupling a capillary to another component of a fluidic device, wherein the ferrule comprises a ferrule body, wherein the ferrule body has a lumen configured for receiving at least a part of the capillary, wherein the ferrule body has a tapering front part configured for forming a sealed connection with a housing of the fitting, wherein a back side of the tapering front part has an annular undercut.

19 Claims, 5 Drawing Sheets

(56) References Cited

U.S. PATENT DOCUMENTS

| | | | |
|---|---|---|---|
| 5,191,888 A | 3/1993 | Palmer et al. | |
| 5,288,113 A | 2/1994 | Silvis et al. | |
| 5,381,497 A | 1/1995 | Toland et al. | |
| 5,540,464 A * | 7/1996 | Picha | G01N 30/6039 210/198.2 |
| 5,569,222 A | 10/1996 | Haselhorst et al. | |
| 5,595,406 A * | 1/1997 | Warchol | F16L 39/00 285/319 |
| 5,669,637 A * | 9/1997 | Chitty | F16L 33/224 285/342 |
| 5,720,734 A | 2/1998 | Copenhaver et al. | |
| 5,988,700 A | 11/1999 | Prichard | |
| 6,056,331 A * | 5/2000 | Benett | F16L 19/02 285/334.4 |
| 6,086,574 A | 7/2000 | Carroll et al. | |
| 6,102,449 A | 8/2000 | Welsh | |
| 6,131,963 A * | 10/2000 | Williams | F16L 19/10 285/343 |
| 6,575,501 B1 * | 6/2003 | Loy, Jr. | F16L 19/0218 285/339 |
| 6,629,708 B2 * | 10/2003 | Williams | F16L 19/103 285/342 |
| 6,926,313 B1 * | 8/2005 | Renzi | B01J 19/0093 285/342 |
| 7,048,448 B2 | 5/2006 | Rosenberg et al. | |
| 7,066,496 B2 * | 6/2006 | Williams | F16L 19/14 285/249 |
| 7,108,288 B2 * | 9/2006 | Bennett | F16L 19/14 285/249 |
| 7,118,290 B2 | 10/2006 | Ishigami et al. | |
| 7,316,777 B2 * | 1/2008 | Loy, Jr. | B01L 3/565 210/198.2 |
| 7,367,595 B2 * | 5/2008 | Williams | F16L 19/103 285/342 |
| D574,490 S | 8/2008 | Patzer | |
| 7,527,436 B2 | 5/2009 | Hodge et al. | |
| 7,708,470 B2 | 5/2010 | Cooke et al. | |
| 7,735,878 B2 * | 6/2010 | Keene | F16L 15/009 285/332 |
| 7,878,716 B2 | 2/2011 | Morgenstern | |
| D639,657 S | 6/2011 | Hoyt et al. | |
| 8,038,180 B2 * | 10/2011 | Williams | F16L 19/06 285/343 |
| 8,128,131 B2 * | 3/2012 | Barnett | F16L 7/02 285/332 |
| 8,579,870 B2 | 11/2013 | Willis et al. | |
| 8,764,316 B1 | 7/2014 | Barnette et al. | |
| 8,783,486 B1 | 7/2014 | Hoyt et al. | |
| D735,853 S * | 8/2015 | Pa | D24/129 |
| 2003/0107216 A1 * | 6/2003 | Gibson | F16L 19/103 285/353 |
| 2003/0178848 A1 | 9/2003 | Williams | |
| 2004/0037509 A1 | 2/2004 | Wisecarver | |
| 2004/0247255 A1 | 12/2004 | Rosenburg et al. | |
| 2006/0138774 A1 * | 6/2006 | Williams | F16L 19/06 285/339 |
| 2008/0054626 A1 * | 3/2008 | Bearer | F16L 19/065 285/39 |
| 2008/0232742 A1 | 9/2008 | Cooke et al. | |
| 2009/0295156 A1 * | 12/2009 | Ford | G01N 30/6039 285/384 |
| 2010/0148501 A1 | 6/2010 | Bennett | |
| 2011/0081117 A1 | 4/2011 | Drake | |
| 2011/0107823 A1 | 5/2011 | Dehmer | |
| 2011/0173798 A1 | 7/2011 | Miller et al. | |
| 2011/0181042 A1 | 7/2011 | Clason | |
| 2011/0198842 A1 | 8/2011 | Murphy | |
| 2013/0140815 A1 * | 6/2013 | Arstein | F16L 19/061 285/386 |
| 2014/0110933 A1 * | 4/2014 | Jencks | F16L 19/0206 285/212 |
| 2015/0097368 A1 * | 4/2015 | Williams | F16L 19/10 285/332 |
| 2015/0160416 A1 * | 6/2015 | Gibson | C23C 8/04 385/72 |
| 2015/0198567 A1 * | 7/2015 | Buerger | F16L 21/035 285/347 |
| 2015/0369403 A1 * | 12/2015 | Cormier | G01N 30/6026 285/357 |
| 2016/0146383 A1 * | 5/2016 | Gibson | F16L 19/103 285/382.4 |

FOREIGN PATENT DOCUMENTS

| | | | | |
|---|---|---|---|---|
| CN | 101809350 A | 8/2010 | | |
| CN | 102405468 A | 4/2012 | | |
| FR | 1289628 A | 4/1962 | | |
| GB | 1164126 A | 9/1969 | | |
| GB | 2 482 175 A | 1/2012 | | |
| WO | 2011076244 A1 | 6/2011 | | |
| WO | WO 2012009726 A1 * | 1/2012 | | G01N 30/6039 |
| WO | 2014007820 A1 | 1/2014 | | |

OTHER PUBLICATIONS

Selected documents from the European prosecution of related EPO application No. 12738306.5 (2015/2016; 18 pages).*

Oct. 5, 2016 Response filed in related European application No. 12738306.5 (14 pages).*

Office action dated Dec. 11, 2015 from related Chinese Patent Application No. 201280074520.6.

International Search Report for International Application No. PCT/US2012/045524 mailed on Mar. 6, 2013.

European Examination Report dated Jun. 16, 2016 from related European Application No. 12 738 306.5-1554.

Chinese Office action dated Aug. 19, 2016 from related Chinese Application No. 201280074520.6.

* cited by examiner

Fig. 5

SINGLE-PIECE FERRULE WITH UNDERCUT TAPERING PART

RELATED APPLICATIONS

This application is the national stage of International Application No. PCT/US2012/045524, filed Jul. 5, 2012, titled "SINGLE-PIECE FERRULE WITH UNDERCUT TAPERING PART," the content of which is incorporated herein by reference in its entirety.

BACKGROUND ART

The present invention relates to a ferrule for a fitting for a fluidic device.

In liquid chromatography, a fluidic phase containing a fluidic analyte may be pumped through a column comprising a material which is capable of separating different components of the fluidic analyte. Such a material, so-called beads which may comprise silica gel that can be chemically modified, may be filled into a column tube which may be connected to other elements (like a control unit, containers including sample and/or buffers). During operation, such columns may be subjected to high pressures of, for instance, up to 600 bar (60 MPa, or about 8,702 pounds per square inch) and more. The liquid chromatographic process includes mixing of the fluidic phase and analyte and introducing this mixture into the column tube with a continuous flow. The different solutes within the sample interact differently with the silica gel in the column and thus move at different speeds through the column resulting in separations of the solutes. The separated solutes may then be detected by various detectors.

In gas chromatography, solutes or components of an analyte sample are separated. Generally, a gas chromatography device includes a downstream column system, including one or more capillary columns for separating the solutes. The columns are typically made of metal, glass or quartz with a thin-film coating or stationary phase which may be connected to other elements (like a pressure control unit, gas supply units and sample containers). The gas chromatography process includes mixing the analyte sample with a carrier gas, such as hydrogen or helium, and introducing the sample/carrier gas mixture into the column(s) using a continuous flow. Various solutes within the sample interact differently with the stationary phase, and thus move at different speeds through the column(s), resulting in separation of the solutes. The separated solutes may then be detected by various detectors or provided as input to a mass spectrometer device, for example.

Fittings for coupling different components, such as separation columns and conduits, of fluidic devices, such as gas chromatography devices or liquid chromatography devices, are commercially available and are offered, for instance, by the company Swagelok (see for instance http://www.swagelok.com).

Conventionally, multiple ferrule systems (for instance U.S. Pat. No. 7,108,288, U.S. Pat. No. 7,367,595, US 2009/0295156, U.S. Pat. No. 7,735,878) are used. Single ferrule systems (for instance U.S. Pat. No. 6,056,331, U.S. Pat. No. 5,669,637, U.S. Pat. No. 6,575,501, U.S. Pat. No. 7,316,777, WO 2012/009726, U.S. Pat. No. 3,893,716, U.S. Pat. No. 4,205,417, U.S. Pat. No. 4,586,731, U.S. Pat. No. 6,926,313, U.S. Pat. No. 7,066,496, U.S. Pat. No. 8,038,180, US 2008/0054626, U.S. Pat. No. 6,131,963, U.S. Pat. No. 6,629,708) can be used to simplify the design.

Specifically, connection systems for glass capillaries as used in gas chromatography are disclosed in, U.S. Pat. No. 8,128,131 and WO 2001/73338.

For making a leak-free connection, a ferrule may be used together with a corresponding nut or housing. Such systems are disclosed in U.S. Pat. No. 5,595,406, U.S. Pat. No. 6,102,449, U.S. Pat. No. 5,540,464, U.S. Pat. No. 5,288,113.

There are tough requirements regarding sealing performance and mechanical stability of a fitting of fluidic measurement devices.

DISCLOSURE

It is an object of the invention to provide both reliable sealing performance and high mechanical stability when forming a fluidic coupling between different components of a fluidic device.

According to an exemplary embodiment of the present invention, a single-piece ferrule (i.e. a ferrule consisting of one body only) for a fitting (or a connector) for coupling a capillary (such as a tubing having an inner fluid lumen) to another component (for instance another capillary or another conduit) of a fluidic device (such as a gas chromatography device) is provided, wherein the ferrule comprises a ferrule body which has a lumen configured for receiving at least a part of the capillary, wherein the ferrule body has a tapering front part (wherein the term "front" may refer to an end of the fitting facing the other component) configured for forming a sealed connection with a housing (which may be formed of a male piece and a female piece) of the fitting, wherein a back side (or rear side) of the tapering front part has an annular undercut (such as a rearward ring-shaped notch, groove, or indentation).

According to another exemplary embodiment, a fitting for coupling a capillary to another component of a fluidic device is provided, the fitting comprising a housing (for instance a two-piece housing), and a ferrule having the above-mentioned features, wherein the tapering front part of the ferrule is configured for forming a sealed connection with the housing (particularly when the ferrule is mounted within the housing).

According to yet another exemplary embodiment, a fluidic device for processing a fluidic sample (which may have gaseous and/or liquid components) is provided, the fluidic device comprising a capillary for conducting the fluidic sample, another component (wherein the other component may have a fluidic conduit, such as another capillary or a channel in a substrate) to be coupled to one end of the capillary, a processing element (such as a chromatographic column) coupled to the other end of the capillary and being configured for interacting with the fluidic sample for processing the fluidic sample, and a fitting having the above-mentioned features for coupling the capillary to the other component (particularly for establishing a sealed fluid communication between the capillary and the other component).

According to still another exemplary embodiment, a single-piece ferrule for a fitting for coupling a capillary to another component of a fluidic device is provided, wherein the ferrule comprises a ferrule body. Such a ferrule may be designed by configuring (particularly shaping and/or dimensioning) a lumen of the ferrule body for receiving at least a part of the capillary, configuring (particularly shaping and/or dimensioning) a tapering front part of the ferrule body for forming a sealed connection with a housing of the fitting, and configuring (particularly shaping and/or dimensioning)

an annular undercut of a back side of the tapering front part to thereby adjust frictional contact characteristics between the ferrule and the housing.

According to still another exemplary embodiment, a method of coupling a capillary to another component of a fluidic device by a fitting is provided, wherein the method comprises receiving at least a part of the capillary in a lumen of a ferrule body of a single-piece ferrule of the fitting, and forming a sealed connection between a tapering front part of the single-piece ferrule and a housing of the ferrule, wherein a back side of the tapering front part has an annular undercut.

The ferrule provided according to an exemplary embodiment of the invention allows for a compact design because it is integrally formed as a single piece. Such a ferrule is further basically maintenance-free and user-convenient, because a user does not have to handle many parts. Beyond this, such a ferrule reliably ensures a sealed connection between a capillary accommodated within the lumen of the ferrule on the one hand and a connected fluidic conduit of another component on the other hand. This other fluidic component can be brought in fluid communication with the lumen when the ferrule is mounted in the housing of the fitting. When the ferrule is mounted in such a housing (for example is received in a fitting accommodation space delimited by a male piece and a cooperating female piece of the housing), a compression force applied by the housing from all sides to the ferrule may seal the ferrule to the housing and may at the same time seal the capillary to the ferrule. A ring groove or annular undercut at a rear side of the ferrule allows for precisely adjusting the wall frictional contact properties to allow material to flow inside the recess of the annular undercut during the compression to obtain a large range of constriction. Advantageously, the undercut or notch in the front part of the ferrule reduces the material of the ferrule on which the compression force must act.

Next, further exemplary embodiments of the ferrule will be explained. However, these embodiments also apply to the fitting, the fluidic device and to the methods.

A fluid separation column capillary (or even at least a part of a corresponding separation column) may extend through a part of or even through the entire ferrule. In such an embodiment, the sealing area may be on the tip of the ferrule. The for instance V-shaped rib may have the purpose to reduce the bulk stiffness.

In an embodiment, the annular undercut has a triangular shape in a cross-section along a plane containing an extension direction of the lumen. The triangle may have rounded edges and may slightly deviate from a precise triangular shape. Such a shape maintains high mechanical stability while at the same time providing for a sufficiently large gap for receiving material during the compression procedure.

In an embodiment, the tapering front part has a front face (such as a circular ring which may be rounded), a back face (such as a circular ring having larger area than the circular ring forming the front face) and a lateral (for instance conical) area or surface tapering from the back face towards the front face. The annular undercut may then be formed as a circumferential recess (which may taper along an extension direction of the lumen) extending into the back face along or parallel to an extension direction of the lumen. Thus, the annular undercut may be located between an exterior collar and a central longitudinal sleeve-like portion of the front of the ferrule.

In an embodiment, the tapering front part has a conical section located between a rounded tip and a beaked (or acuate) section. The beaked section may pass (or change over) into the annular undercut. The conical section may be aligned or may abut against a cooperating surface of the housing, particularly of a female part of such a housing. By configuring the back of the front part with a beaked section, an annular wing-like structure is provided which continuously becomes mechanically weaker towards an end of the beaked section. Therefore, it is possible that particularly this end can assume basically any shape and can also be pressed in hollow spaces within the housing upon applying a compression force to the ferrule.

In an embodiment, the annular undercut is configured to be radially reduced in size upon compressing the ferrule for forming the sealed connection with the housing. The undercut hence provides an empty space into which compressed material can be pushed without the risk of deteriorating the sealing performance.

In an embodiment, the ferrule body has a tapering middle part directly juxtaposed to the annular undercut of the tapering front part. The tapering front part may taper steeper than the tapering middle part. Thus, the part of the ferrule directly abutting against the housing may be slanted with a larger slope than the tapering middle part. The resulting pronounced arrow-like shape of the front part also promotes a centering of the ferrule during assembly within the housing.

In an embodiment, a neck angle is formed as an intersection angle between a surface of the tapering middle part and a surface of a tapering portion within the annular undercut adjacent to the beaked section. Hence, a neck angle is defined by an intersection between a first line or plane being tangent to the tapering middle part and a second line or plane being tangent to a tapering surface portion within the undercut adjoining to the beaked section. Therefore, two basically planar or linear sections may define such a neck angle by a virtual intersection thereof. The presence of such a neck angle serves to reduce or even eliminate the wall frictional contact to allow the material to flow inside the void area for a larger range of constriction.

In an embodiment, the neck angle is designed to be an acute neck angle, particularly in a range between about 5° and about 45°, more particularly in a range between about 15° and about 35°, and even more particularly in a range between about 20° and about 30°. For instance, the neck angle may be about 25°. The given ranges have turned out to be a proper trade-off between, on the one hand, sufficient freedom of material of the ferrule to flow into the undercut during compression and, on the other hand, a sufficient rigidity of the ferrule required to provide a proper sealing.

In an embodiment, the ferrule body has a back part with a rear surface configured for being compressed by a housing of the fitting to thereby transmit a sealing forward force to the front part for sealing the front part to the housing and to the capillary. Therefore, the ferrule may be configured so that, when the ferrule is mounted in the housing, the housing presses from a backward position towards a back face of the ferrule to thereby transmit a compression force in a radial direction and in an axial direction forwardly in order to provide for a proper sealing between the ferrule and the housing as well as between the ferrule and the capillary.

In an embodiment, the back part has a larger diameter (in a direction perpendicular to the extension of the lumen and the capillary) than the front part. When the back part has a relatively large extension, a sufficiently large rear surface area is provided as well allowing to transmit a large compression force to the ferrule. At the same time, the smaller area at the arrow-shaped front portion of the ferrule allows for a small sealing surface to which the sealing force is distributed thereby providing for an efficient sealing.

In an embodiment, the back part has a basically cylindrical shape. With such a rotationally symmetric geometry it is possible to transfer also the compression force in a symmetric way towards the ferrule.

In an embodiment, the back part has at least one annular groove, particularly a plurality of annular grooves, extending from an outer circumferential surface of the back part towards the—but still spaced with regard to the—lumen of the ferrule body. If compression pressure is applied to a back of the ferrule, the annular grooves may be compressed. Hence, such a groove or grooves may reduce bulk stiffness during compression to weaken the sensitivity of forces to the construction. The notch or notches in the back part removes additional material from the ferrule, thereby further reducing the amount of material to be moved during compression.

Particularly the undercut in the back of the front part in combination with the at least one groove in the back part of the ferrule synergetically contribute to a weight reduction and a high mechanical flexibility of the ferrule whilst allowing material of the ferrule to flow into the resulting voids during compression. Particularly when manufacturing the ferrule from a metallic material, these advantages may be further combined with a high mechanical robustness and a reliable sealing meeting the requirements of modern chromatography applications.

In an embodiment, at least one annular groove is V-shaped. The tip of the V thereby points towards the lumen so that the reduction of this stiffness is larger at an external circumference of the ferrule. A V-shape has turned out to be a preferred shape since it promotes stiffness of the ferrule and does not easily collapse upon stress acting thereon.

In an embodiment, the at least one annular groove is configured to be axially reduced in size upon compressing the ferrule. Therefore, also the back part has, thanks to the one or more ring-shaped grooves, a reduced rigidity allowing material being compressed to flow into such empty spaces.

The sections of the back part being separated by the one or more grooves may have the same or different thicknesses along an extension direction of the lumen or the capillary. Furthermore, the sections of the back part being separated by the one or more grooves may have the same or different lateral extensions (for instance diameter) perpendicular to the extension direction of the lumen or the capillary.

In an embodiment, the ferrule comprises a tapering transition portion connecting the tapering middle part to the back part. Hence, two portions of different tapering steepness can be located between front part and back part. A border between the tapering transition portion and the tapering middle part may show a kink or may be continuous in terms of slope.

In an embodiment, the tapering transition portion tapers steeper than the tapering middle part. This geometry emphasizes the arrow-shaped geometry of the ferrule.

In an embodiment, the entire ferrule is made of a single material only. This prevents mechanical damage or weak points concerning sealing performance between different portions of the ferrule body made of different materials.

In an embodiment, the ferrule body comprises or consists of a metal, particularly a soft metal. For instance, the ferrule body may be made of steel which, particularly in conjunction with the undercut and the grooves, provides sufficient mechanical stability to allow material to flexibly flow in empty spaces while at the same time ensuring a reliable sealing in the front section. Other suitable materials are stainless steel or brass. Such metallic materials are preferred since they can be provided cleaner than for instance plastic ferrules. Furthermore, metallic ferrules can be operated with many alternating sequences of compressing and loosening without experiencing undesired plastic deformation. Alternative materials for ferrules which may be used as well but being less preferred than metal are plastic ferrules filled with reinforcing carbon filling.

In an embodiment, the lumen has a first cylindrical lumen section having a first diameter, a second cylindrical lumen section having a second diameter differing from the first diameter, and a tapering lumen section connecting the first cylindrical lumen section to the second cylindrical lumen section. The first cylindrical lumen section may be configured for loosely (particularly with a gap in between) receiving part (particularly a middle part) of the capillary. The second cylindrical lumen section may be configured for sealingly receiving another part (particularly a front part) of the capillary. In an embodiment, the first diameter is larger than the second diameter.

However, it is also possible that the lumen of the ferrule has a continuous diameter along its entire extension. The capillary may extend along the entire lumen.

In an embodiment, the configuring is performed at least partially by modeling of stresses acting on the ferrule during compression with the housing. Therefore, the mechanical load acting on the ferrule and parts thereof can be modelled or simulated, thereby allowing to design a ferrule with advantageous effects in terms of sealing performance responsive to the application of a compression force.

Next, further exemplary embodiments of the fitting will be explained. However, these embodiments also apply to the ferrule, the fluidic device and to the methods.

In an embodiment, the housing comprises a male piece and a female piece, wherein the ferrule is to be compressed between the male piece and the female piece when being assembled. The term "male piece" denotes a piece of the housing which has a projection which may protrude into a correspondingly shaped recess of the female piece while maintaining a ferrule accommodation space between male piece and female piece. Correspondingly, the term "female piece" denotes a piece of the housing which has a recess into which a correspondingly shaped protrusion of the male piece may be inserted while maintaining a ferrule accommodation space between male piece and female piece. When male piece and female piece are connected to one another, the ferrule accommodation space remains in their interior which is shaped in accordance with the a shape of the ferrule. Therefore, when the ferrule is inserted between male piece and female piece and these three pieces are mounted together, a remaining recess is very small or even zero.

For instance, some type of proprietary male/female nut may be used to make a leak free connection, see for instance U.S. Pat. No. 5,595,406 or U.S. Pat. No. 6,102,449.

In an embodiment, the male piece and the female piece have cooperating threads to be screwed to one another upon assembling the male piece and the female piece. For example, the male piece may have an external thread and the female piece may have a corresponding internal thread. By simply applying a screwing operation, the male piece may be screwed onto the female piece with the ferrule being compressed in between.

In an embodiment, the capillary of the fitting is made of glass or fused silica. The disclosed ferrule geometry is particularly appropriate for a brittle tubing made of fused silica or glass, as used advantageously in gas chromatography applications. Thus, in view of the annular undercut and the one or more recesses in the back part, compression forces may be efficiently reduced so that the force acting on a glass or fused silica tubing is sufficiently small to avoid damage.

In an embodiment, the capillary has a lumen having a diameter of less than about 1.0 mm (about 0.039 inch), particularly of less than about 0.2 mm (about 0.008 inch). Therefore, the ferrule is appropriate for use in microfluidic or even nanofluidic applications.

Next, further exemplary embodiments of the fluidic device will be explained. However, these embodiments also apply to the ferrule, the fitting and to the methods.

In an embodiment, the processing element is integrally formed with the capillary. For instance, the capillary may form part of the processing element and may extend with a free end beyond it. This free end may then be fluidicly coupled to the other component by the fitting.

Such a processing element may be any fluidic member which is capable of acting upon the fluidic sample. The processing element may advantageously be a chromatography separation column, but may also be a fluidic mixer, a fluidic valve, a sample injector, etc.

In an embodiment, the processing element is configured for retaining the fluidic sample being a part of a mobile phase and for allowing other components of the mobile phase to pass the processing element. Therefore, the processing element may have the capability to separate the different components or fractions of the fluidic sample due to a different degree of interaction between different fractions of the fluidic sample with material of the processing element.

In an embodiment, the processing element comprises a separation column. The processing element may particularly comprise a chromatographic column, more particularly a gas chromatography column or a liquid chromatography column, for separating components of the fluidic sample. The functioning of the chromatographic separation column is based on a different interaction between different components of the fluidic sample with materials such as beads within the chromatographic column.

In an embodiment, the fluidic device is configured as a chromatography device, particularly as a gas chromatography device or a liquid chromatography device. However, the present invention is not limited to chromatographic applications but can be used in all types of fluidic systems.

BRIEF DESCRIPTION OF DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs.

The illustration in the drawing is schematic.

In the following, some considerations of the present inventor with regard to ferrules in chromatographic applications will be explained, based on which exemplary embodiments of the invention have been developed.

Ferrules are not a stand-alone product and require, in use, various nuts and some type of tubing for making leak free fluid connections. Metal ferrule products may be used for making connections to metal tubing. These connections have a metal to metal seal formed from the ferrule and some connecting fitting. To make the seal, the ferrule is compressed on the metal tubing thereby constricting the outside of the tubing at the ferrule contact points. This type of connection is however not always suitable for more brittle tubing like fused silica or glass tubing in gas chromatography applications, which may break when a ferrule of this type constricts on the outside of the tubing. Also, conventional metal ferrules do not always constrict for re-sealable connections to metal tubing, more geared to liquid chromatography applications.

Connection systems for glass (or other brittle) capillaries face the challenge of making leak free connections between glass columns to a metal connection, particularly in gas chromatography. Vespel and graphite/Vespel and graphite ferrules can be used for this application. Vespel forms a good seal but can become loose when exposed to temperature cycling. Graphite/Vespel is more appropriate for temperature cycling applications, but does show some shrinkage with time resulting in leakage and is somewhat porous. Graphite is easily deformed and forms a reliable seal but is porous which can allow atmospheric gases to defuse into the chromatographic system. Graphite also can easily adsorb contaminants that can be observed during gas chromatography use at elevated temperatures.

In view of the foregoing, exemplary embodiments implement a soft metal ferrule for connecting fused silica capillary columns to the inlet and detector of a gas chromatography system. This has the advantage that when the ferrule deforms under tightening of a male/female nut combination the seal is leak tight or cannot be over-tightened to prevent the glass column to break. This results in an improved ferrule that deforms under tightening such that the brittle glass column does not break.

Figure 1:
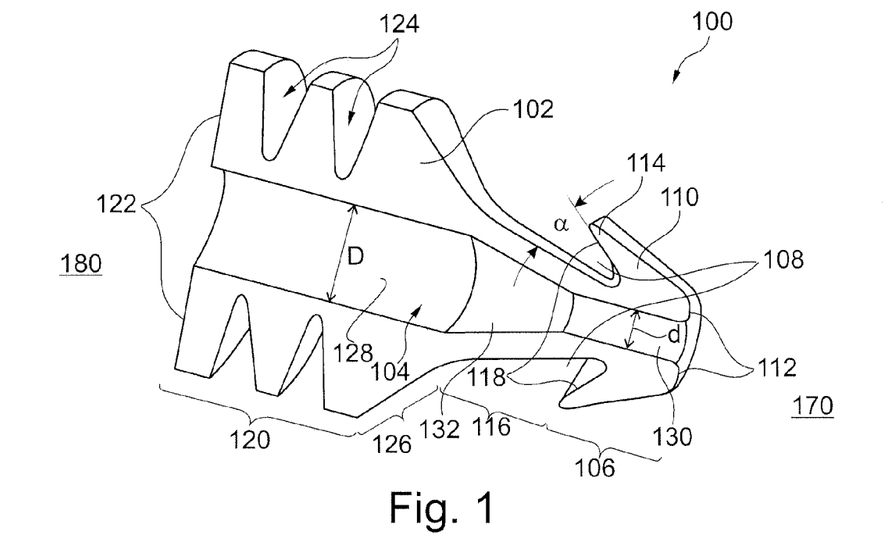
FIG. 1 illustrates a three-dimensional view of a cross-section of a ferrule according to an exemplary embodiment.

FIG. 1 illustrates a one-piece ferrule 100 according to an exemplary embodiment of the invention. A cone end of the ferrule 100 is denoted with reference numeral 170, whereas a compression end of the ferrule 100 is denoted with reference numeral 180. A further feature is an angled area (see "a") between the cone end 170 and the compression end 180 referred to here as the neck.

Figure 2:
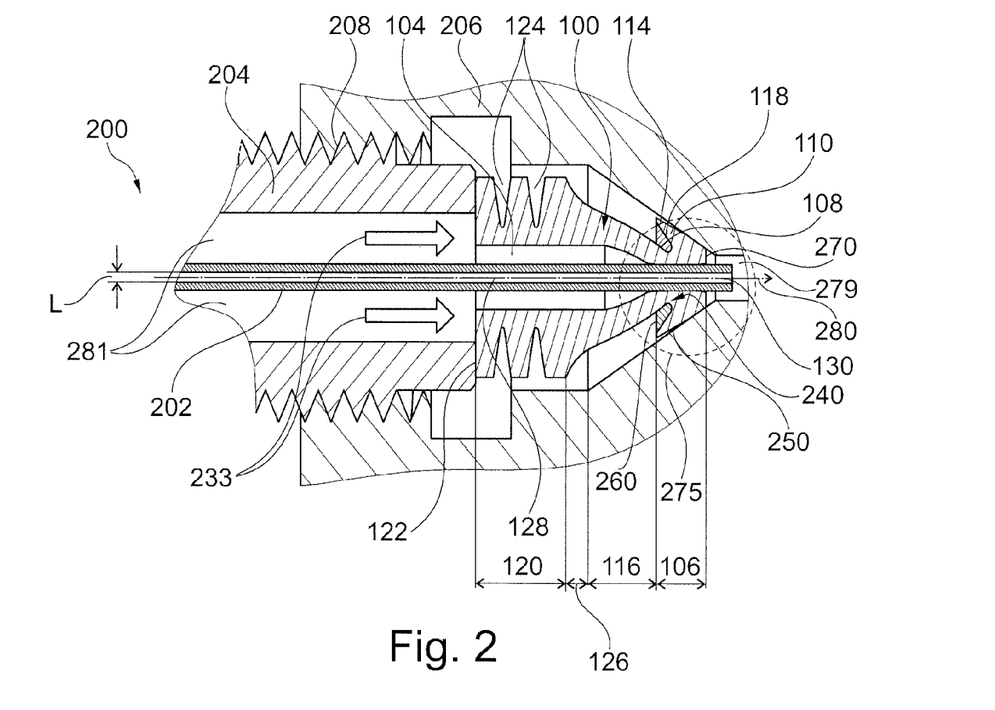
FIG. 2 illustrates a cross-sectional view of an assembled fitting according to an exemplary embodiment.

A fitting 200 according to an exemplary embodiment is shown in FIG. 2, wherein the single piece ferrule 100 of FIG. 1 forms part of the fitting 200. Adjacent to the left hand side of FIG. 2 is a chromatographic column (not shown) which is coupled to column capillary 202. Adjacent to the right hand side of FIG. 2 is a detector (not shown) which is coupled to a conduit 279. Hence, fitting 200 may form part of a chromatographic separation device.

The ferrule 100 is configured for coupling a brittle capillary 202 (for instance made of glass or fused silica) of a chromatographic column to another component such as conduit 279 which is, in turn, coupled to a chromatographic detector (not shown in FIG. 2). The ferrule 100 consists of a single ferrule body 102 integrally formed from a single material, in the shown embodiment stainless steel. A rotationally symmetric recess is formed centrally within the rotationally symmetric ferrule body 102 to thereby constitute a lumen 104. A front part of the capillary 202 is to be received in the lumen 104 when assembling the fitting 200.

As can be taken best from FIG. 1, the lumen 104 has a first cylindrical lumen section 128 which has a first diameter D. Furthermore, the lumen 104 has a second cylindrical lumen section 130 having a second diameter d. D is larger than d. A conically tapering lumen section 132 connects the first cylindrical lumen section 128 to the second cylindrical lumen section 130, i.e. provides for a continuous transition. The diameter tapering transition from lumen 104 to section 132 to section 130 helps in channeling the plastic deformation flow of the material to help in constricting the diameter d of section 130 in the area of an undercut 108.

As can furthermore be taken from the three-dimensional cross-sectional view of the ferrule 100 in FIG. 1, the ferrule body 102 has a tapering front part 106. When being assembled within a housing (see male piece 204, and female piece 206 in FIG. 2) of the fitting 200, the tapering front part 106 of the ferrule 200 contributes to a sealed connection. As can furthermore be taken from FIG. 1, a back side of the tapering front part 106 has an annular undercut 108. The annular undercut 108 is a ring-shaped recess which tapers inwardly in a direction from the left-hand side in FIG. 1 to the right-hand side of FIG. 1. The terms "front" and "back" refer to a mounting and extension direction of the capillary 202 within the lumen 104 of the ferrule body 102.

When the ferrule 100 is mounted in the housing 204, 206, radially and axially exerted compression forces act on the ferrule 100. If these forces are transferred to a brittle tubing such as a fused silica or glass capillary 202, the latter may break. The same holds for brittle fluidic components to be connected to the fitting 200 shown in FIG. 2. The empty space provided by the basically V-shaped undercut 108 at the back side of the tapering front part 106 of the ferrule 100 allows material to be relocated or accommodated within this space, thereby reducing the forces acting on the various components.

As can be furthermore taken from FIG. 1, the tapering front part 106 has a conical section 110 with an external surface showing a constant slope. The conical section 110 is located between a rounded tip 112 on the cone end 170 and a beaked section 114. The beaked section 114 passes into the annular undercut 108. The annular undercut 108 is configured to be reduced in size when the ferrule 100 is compressed for forming the sealed connection within the housing 204, 206.

Furthermore, a tapering middle part 116 adjacent to the annular undercut 108 of the tapering front part 106 is provided as well. The tapering front part 106 however tapers steeper than the tapering middle part 116.

FIG. 1 also shows neck angle α as an angle formed between linear extrapolations of the tapering middle part 116 and a tapering surface portion 118 between the beaked section 114 and the deepest position of the pocket forming the annular undercut 108. For example, the neck angle α may be 25°. The neck angle α allows to adjust frictional properties of the ferrule 100 with regard to a wall of a surrounding housing 204, 206, thereby also adjusting the properties of the ferrule 100. It can therefore be adjusted to which extent material can flow into the recessed area or undercut 108 for a large range of constriction.

The ferrule body 102 furthermore has a back part 120 with a circular rear surface 122 at the compression end 180. A compression force is exerted to the back part 120 when the ferrule body 102 is compressed by the housing 204, 206 of the fitting 200 upon assembly to thereby transmit a sealing forward force to the front part 106. The force applied to the rear surface 122 is oriented parallel to the extension of the capillary 202. However, due to the slanted or tapering configuration of the front part 106 of the ferrule 100, this compression force is split into a longitudinal/axial component and into a radial force component. Therefore, a proper sealing of the front part 106 of the ferrule 100 against the corresponding metal surface of the housing 204, 206 can be guaranteed as well as a proper sealing of the ferrule 100 against the capillary 202. Since the back part 122 has a larger radial extension than the front part 106, i.e. a larger extension in a vertical direction according to FIG. 2, a high compression force may be applied to the large area of the rear surface 122 which is then distributed over a significantly smaller front surface of the ferrule 100 abutting against the housing 204, 206 to provide for the sealing.

The back part 122 has a cylindrical shape with two ring-shaped or annular grooves 124 spaced along an extension of the capillary 202. By the provision of these V-shaped grooves 124, the back part 122 of the ferrule 100 behaves like a spring-like element, wherein material of the ferrule 100 and/or connected members can be relocated into the V-shaped grooves 124 when applying pressure to the rear surface 122 of the back part 120.

A tapering transition portion 126 connects the tapering middle part 116 to the back part 120. As can be taken from FIG. 1, the tapering transition portion 126 tapers steeper than the tapering middle part 116, i.e. with a higher slanting angle relative to a horizontal extension or an extension of the capillary 202.

The entire ferrule body 102 is made of homogeneous stainless steel. Since only one material is used for forming the entire ferrule 100, no problems with different physical properties (such as thermal expansion properties or responses to applied compression forces) occur.

FIG. 2 shows the ferrule 100 of FIG. 1 assembled in a housing 204, 206. The housing 204, 206 consists of a male piece 204 having an external thread 208 and a female piece 206 having a corresponding inner thread 208. For assembling the fitting 200, the ferrule 100 is placed in a recess of the female piece 206. The capillary 202 may be already inserted into the lumen 104 of the ferrule 100. Subsequently, the male piece 204 may be screwed onto the female piece 206, thereby forming a screw connection at the corresponding threads 208 (reference numeral 281 denotes an empty space). At the same time, during screwing, the ferrule 100 is pressed forwardly, i.e. according to FIG. 2 to the right-hand side, so that the cone-shaped surface of the front part 106 of the ferrule 100 is pressed against a correspondingly shaped surface portion of the female part 206. The tapering angles of the interior metal surface of the female piece 206 and the external surface of the front part 106 may have a slightly different slanting angle or may have a slightly different steepness, which may improve the sealing performance. A force is then applied by the male piece 204 to the back face 122 of the back part 120. Due to the geometry of the ferrule 100, this force is applied to the sealing area between the female piece 206 and the ferrule 100, i.e. in a longitudinal and radial direction, and also compresses the ferrule 100 circumferentially against the capillary 202. An inner diameter L of the capillary 202 has a dimension of 0.1 mm (or about 0.004 inch). For gas chromatography, this dimension L (inside diameter of the capillary 202 as shown in FIG. 2), is for instance ranging from 0.025 mm to 0.530 mm (or from about 0.001 inch to about 0.021 inch). The outside diameter of the capillary 202 corresponding to ferrule inside diameter d of lumen 130, is for instance ranging from 0.135 mm to 0.76 mm (or from about 0.005 inch to about 0.030 inch).

As can be taken from FIG. 2, the annular undercut 108 has a basically triangular shape (shown in FIG. 2 as a hatched area 240) in a cross-section along a plane, i.e. the paper plane of FIG. 2, containing a horizontal extension direction 280 of the lumen 104. The tapering front part 106 has a basically circular front face 270, a (virtual) basically circular back face 260 and a lateral area 250 tapering from the back face 260 towards the front face 270. The annular undercut 108 is formed as a circumferential recess extending into the back face 260 along an extension direction 280 of the lumen 104.

In the following, the mechanical principal of the flexible metal ferrule sealing of FIG. 2 will be explained in further detail. Arrows 233 in FIG. 2 indicate how nut compressive load is applied. No sealing is necessary for the mating surfaces of the male piece 204 and the ferrule 100, i.e. no sealing is necessary at the rear surface 122. Also, no sealing is necessary at the screw connection between the external and internal threads 208. The actual sealing area is denoted with reference numeral 275. The sealing area 275 includes a cylindrical sealing area between mating surfaces of the capillary 202 and of the tapering front part 106 of ferrule 100 (which may be denoted as seal surface column-to-ferrule). The sealing area 275 also includes a cone-shaped sealing area between mating surfaces of the female piece 206 and of the tapering front part 106 of ferrule 100 (which may be denoted as seal surface ferrule-to-housing). The rib grooves or annular grooves 124 serve for ferrule stiffness reduction and identification purposes, but do not need to contribute to sealing.

Figure 3A:
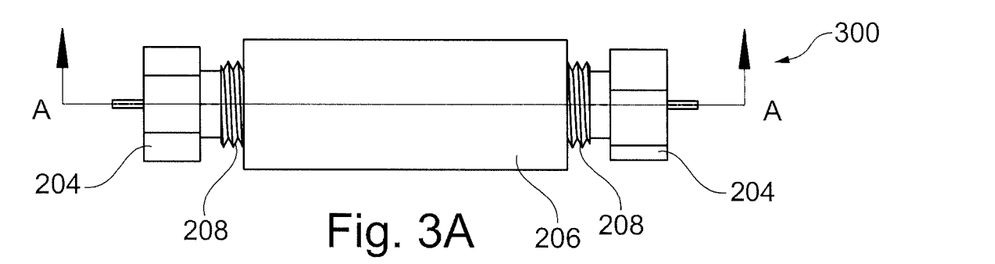
FIG. 3A illustrates a plan view of a double fitting assembled with two ferrules according to an exemplary embodiment.
Figure 3B:
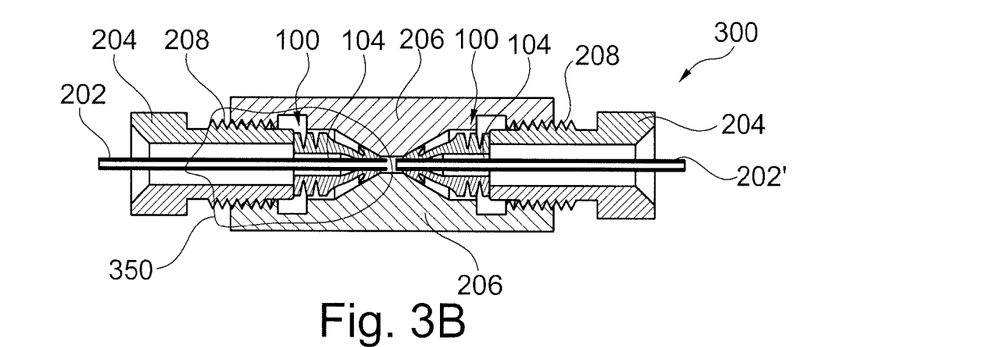
FIG. 3B illustrates a cross-sectional view of the double fitting of FIG. 3A along an axis A-A indicated in FIG. 3A.
Figure 3C:
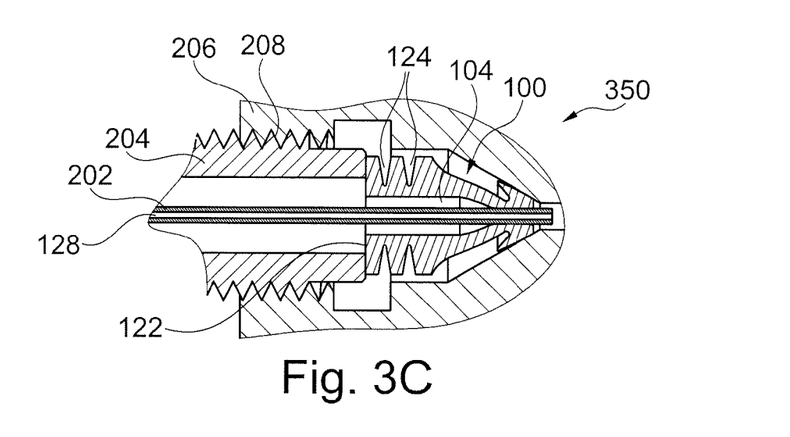
FIG. 3C illustrates a detail of the cross-sectional view of the double fitting of FIG. 3B.

FIG. 3A, FIG. 3B, and FIG. 3C show a double fitting 300 according to an exemplary embodiment of the invention in different views. FIG. 3A illustrates a plan view of the double fitting 300, FIG. 3B illustrates a cross-sectional view (along a line A-A indicated in FIG. 3A) of the double fitting 300 assembled with two ferrules 100, and FIG. 3C illustrates a detail 350 of FIG. 3B.

This double fitting 300 can be considered as a combination of two of the fittings 200 of FIG. 2. However, the female pieces 206 of the two fittings 200 are integrally formed as one piece in FIG. 3A to FIG. 3C. Therefore, two capillaries 202, 202' to be fluidically connected to one another are inserted into respective ferrules 100, 100 which are then, in turn, simply inserted into the recesses of the integrally formed double female piece 206. Subsequently, two male pieces 204 are then screwed into the corresponding recesses of the double female piece 206 for compression. The capillary 202 may be coupled to or may form part of a chromatographic column, whereas the capillary 202' may be coupled to or may form part of another fluidic member such as a detector.

Figure 4:
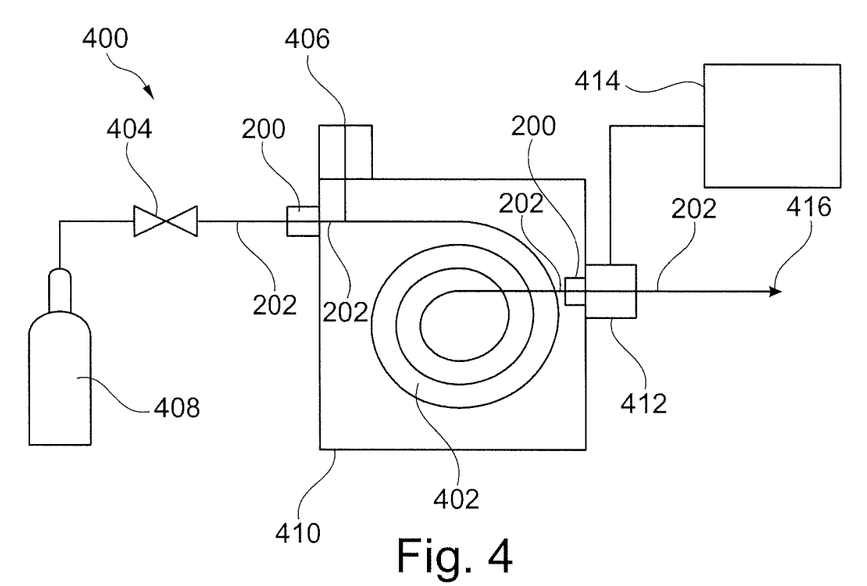
FIG. 4 illustrates a gas chromatography apparatus according to an exemplary embodiment.

FIG. 4 shows a gas chromatography system 400 according to an exemplary embodiment of the invention.

Carrier gas is supplied from a gas bottle 408 via a flow controller 404 and a fitting 200 as shown in FIG. 2 (or a fitting 300 as shown in FIG. 3) into a column oven 410. The column oven 410 includes a gas chromatography separation column 402. The fluidic sample to be separated may be injected via a sample injector 406 into the column oven 410 and into separation column 402. An outlet port of the column oven 410 is connected, via another fitting 200 according to FIG. 2 (or a fitting 300 as shown in FIG. 3), to a detector 412. After separating the components of the fluidic sample in the detector 412, the fluidic sample may be supplied to a waste 416 or to containers for storage. A display device 414 may be provided for displaying the result of the gas chromatography application.

The connections between the various capillaries 202 of the gas chromatography system 400 and the various fluidic components 402, 406, 408, 412 etc. can be provided by the fittings 200 (or fittings 300 as shown in FIG. 3) described above.

Figure 5:
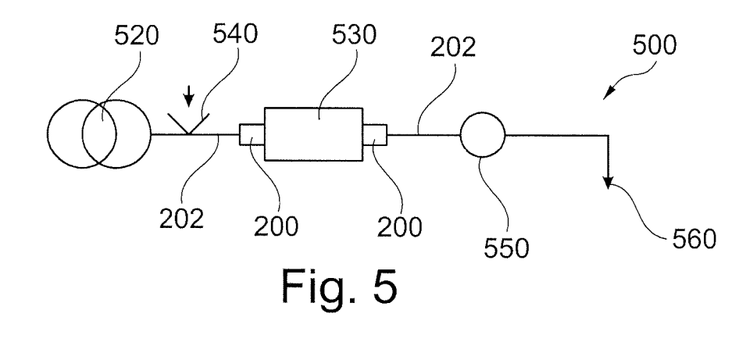
FIG. 5 illustrates a liquid chromatography apparatus according to an exemplary embodiment.

FIG. 5 shows a HPLC (High-Performance Liquid Chromatography) system 500 for a liquid chromatography analysis of a fluidic sample according to an exemplary embodiment.

A pump 520 pumps a mobile phase through a chromatographic column 530 which comprises a stationary phase such as beads made of silica gel. A sample supply unit 540 is arranged between the pump 520 and the chromatographic column 530 in order to inject a fluidic sample into the mobile phase. The stationary phase of the chromatographic column 530 is provided in order to separate components of the fluidic sample which may be pumped through the chromatographic column 530 with a high pressure of, for instance, 2000 bar (200 MPa, or about 29,008 pounds per square inch). A detector 550 detects the separated components of the fluidic sample. A fractioner 560 can be provided to receive the separated components of the fluidic sample, for instance to conduct them into dedicated containers or into a waste container (not shown).

As can be taken from FIG. 5, fittings 200 (or fittings 300) are used to connect an inlet and an outlet of the chromatographic column 530 to a fused silica capillary 202 in a liquid-sealed fashion. Additionally or alternatively, any of the other components shown in FIG. 5 may be connected to such a capillary 202 using a fitting 200 (or a fitting 300).

FIG. 6 to FIG. 12 show ferrules 600, 700, 800, 900, 1000, 1100, 1200 according to exemplary embodiments of the invention mounted on a capillary 202 guided through a lumen 104 of the ferrules 600, 700, 800, 900, 1000, 1100, 1200. Specifically the back end features can change depending on the diameter of the tubing or capillary 202. Particularly grooves 124 are U-shaped (instead of V-shaped) in FIG. 6 to FIG. 12, wherein other shapes are possible as well. There are also changes in the front side possible as well.

Figures 6, 7, 8:
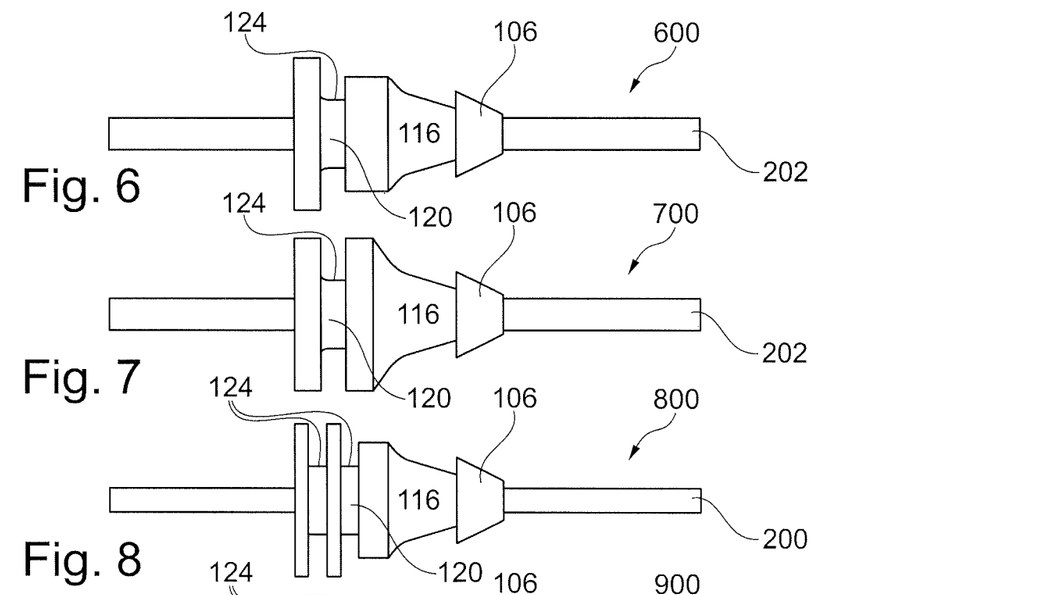
FIG. 6 to FIG. 19 show ferrules with different geometric properties according to exemplary embodiments of the invention.

Ferrule 600 shown in FIG. 6 has a single groove 124 in back part 120 only, wherein the sections of the back part 120 which are separated by the single groove 124 have different diameters (in vertical direction) and different thickness (in horizontal direction).

Ferrule 700 shown in FIG. 7 has a single groove 124 in back part 120 only, wherein the sections of the back part 120 which are separated by the single groove 124 have the same diameter and the same thickness.

Ferrule 800 shown in FIG. 8 has two grooves 124 in back part 120, wherein two of the sections of the back part 120 which are separated by one of the grooves 124 have the same diameter and the same thickness and the other one of the sections (on the right hand side) of the back part 120 has a smaller diameter and a larger thickness.

Figures 9, 10:
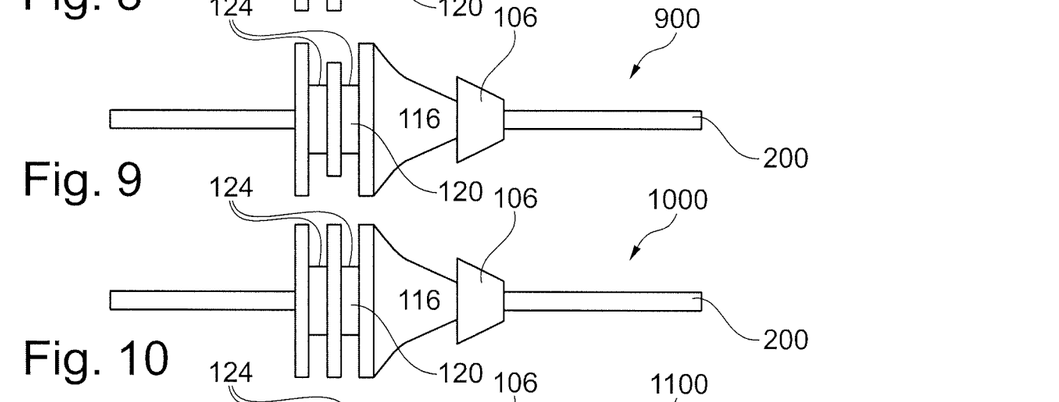

Ferrule 900 shown in FIG. 9 has two grooves 124 in back part 120, wherein two of the sections of the back part 120 have the same diameter and the same thickness and the other one of the sections (in the center) of the back part 120 has a smaller diameter but the same thickness.

Ferrule 1000 shown in FIG. 10 has two grooves 124 in back part 120, wherein all sections of the back part 120 which are separated by the grooves 124 have the same diameter and the same thickness.

Figures 11, 12:
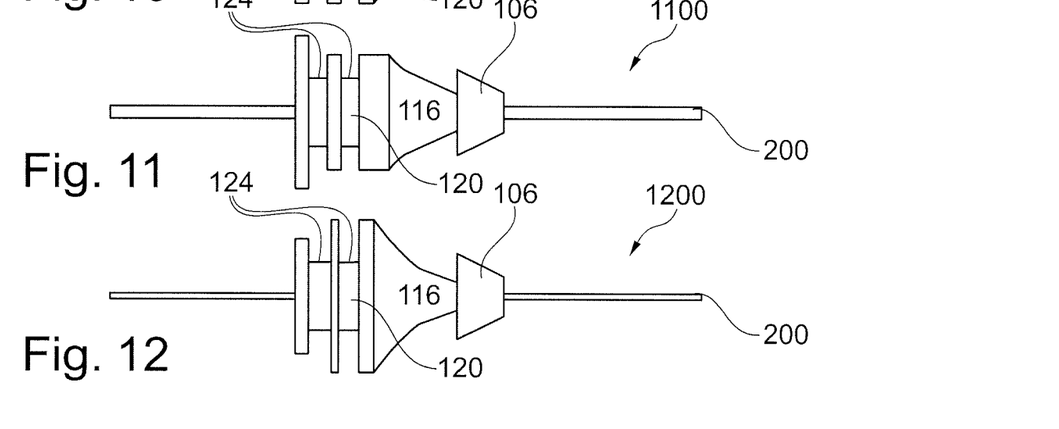
Figure 13:
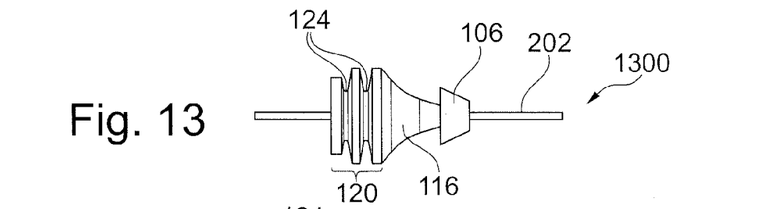
Figure 14:
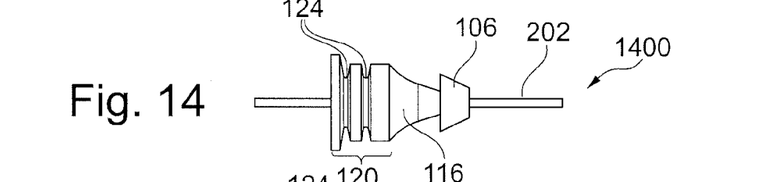
Figure 15:
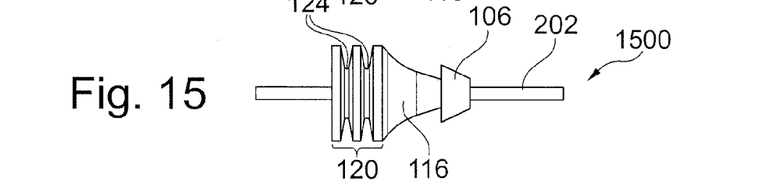
Figure 16:
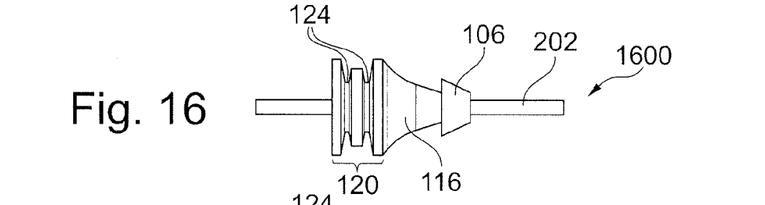
Figure 17:
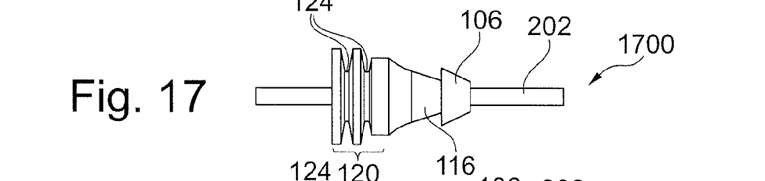
Figure 18:
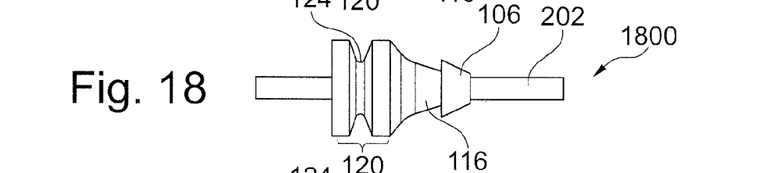
Figure 19:
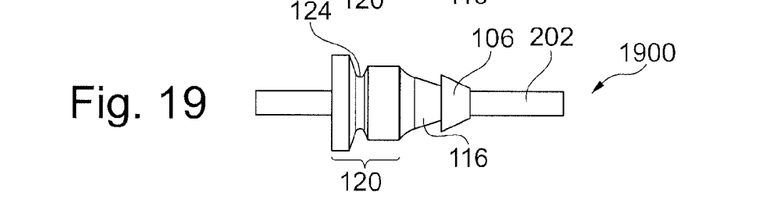

Ferrule 1100 shown in FIG. 11 has two grooves 124 in back part 120, wherein two of the sections (in the middle and on the right hand side) of the back part 120 have the same diameter but different thickness, whereas two of the sections (in the middle and on the left hand side) of the back part 120 have different diameter but the same thickness.

Ferrule 1200 shown in FIG. 12 has two grooves 124 in back part 120, wherein two of the sections (in the middle and on the right hand side) of the back part 120 have the same diameter and different thickness, whereas two of the sections (on the left hand side and on the right hand side) of the back part 120 have different diameter and the same thickness.

FIG. 13 to FIG. 19 show ferrules 1300, 1400, 1500, 1600, 1700, 1800, 1900 according to exemplary embodiments of the invention having V-shaped grooves 124. Apart from this difference regarding the shape of the grooves 124, FIG. 13 basically corresponds to FIG. 12, FIG. 14 basically corresponds to FIG. 11, FIG. 15 basically corresponds to FIG. 10, FIG. 16 basically corresponds to FIG. 9, FIG. 17 basically corresponds to FIG. 8, FIG. 18 basically corresponds to FIG. 7, and FIG. 19 basically corresponds to FIG. 6.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. A single-piece ferrule for a fitting for coupling a capillary to another component of a fluidic device, the ferrule comprising:
a single-piece ferrule body of unitary construction;
wherein the ferrule body comprises a cone end, a compression end, and a lumen extending from the cone end to the compression end and configured for receiving at least a part of the capillary;
wherein the ferrule body comprises a tapering front part at the cone end configured for forming a sealed connection with a housing of the fitting, the tapering front part comprising a front face, a back face, and a lateral surface tapering from the back face toward the front face;
wherein a back side of the tapering front part has an annular undercut formed as a circumferential recess extending into the back face along an extension direction of the lumen and tapering inwardly in a direction extending from the compression end to the cone end; and
wherein the ferrule body has a tapering middle part adjacent to the annular undercut of the tapering front part.

2. The ferrule according to claim 1, wherein the annular undercut has a triangular shape in a cross-section along a plane containing the extension direction of the lumen.

3. The ferrule according to claim 1, wherein the annular undercut is configured to be radially reduced in volume upon compressing the ferrule for forming the sealed connection with the housing.

4. The ferrule according to claim 1, wherein the tapering front part tapers steeper than the tapering middle part.

5. The ferrule according to claim 1, wherein the tapering front part comprises:
a conical section located between a rounded tip and a beaked section, the beaked section passing into the annular undercut.

6. The ferrule according to claim 5, wherein a neck angle (a) is formed as an intersection angle between a surface of the tapering middle part and a surface of a tapering portion within the annular undercut adjacent to the beaked section, and the neck angle ($\alpha$) is selected from the group consisting of: an acute angle; an angle in a range between 5° and 45°; an angle in a range between 15° and 35°; and an angle in a range between 20° and 30°.

7. The ferrule according to claim 1, wherein the ferrule body has a back part with a rear surface configured for being compressed by a housing of the fitting to thereby transmit a forward force to the tapering front part for sealing the tapering front part to the housing and to the capillary.

8. The ferrule according to claim 7, wherein the back part has a configuration selected from the group consisting of:
the back part has a larger radial extension than the tapering front part;
the back part is cylindrical;
the back part has at least one annular groove extending from an outer circumferential surface of the back part towards the and spaced with regard to the lumen of the ferrule body;
the back part has plurality of annular grooves;
the back part has at least one V-shaped or U-shaped annular groove;
the back part has at least one annular groove configured to be axially reduced in volume upon compressing the ferrule; and
a combination of two or more of the foregoing.

9. The ferrule according to claim 1, wherein the ferrule body comprises a back part, and further comprising a tapering transition portion connecting the tapering middle part to the back part.

10. The ferrule according claim 9, wherein the tapering transition portion tapers steeper than the tapering middle part.

11. The ferrule according to claim 1, wherein the lumen has a first cylindrical lumen section having a first diameter (D), a second cylindrical lumen section having a second diameter (d) differing from the first diameter (D), and a tapering lumen section connecting the first cylindrical lumen section to the second cylindrical lumen section.

12. The ferrule according to claim 11, wherein the first cylindrical lumen section has a configuration selected from the group consisting of:
the first cylindrical lumen section is configured for receiving part of the capillary and the second cylindrical lumen section is configured for sealingly receiving another part of the capillary;
the first diameter (D) is larger than the second diameter (d); and
both of the foregoing.

13. A fitting for coupling a capillary to another component of a fluidic device, the fitting comprising:
a housing; and
the ferrule according to claim 1;
wherein the tapering front part of the ferrule is configured for forming the sealed connection with the housing.

14. The fitting according to claim 13, comprising the capillary, wherein the capillary has a configuration selected from the group consisting of:
the capillary comprises glass or fused silica;
the capillary comprises a lumen having a diameter (L) of one of (a) less than 1.0 mm (0.039 inch) and (b) less than 0.2 mm (0.008 inch);
both of the foregoing.

15. The fitting according to claim 13, wherein the housing comprises a male piece and a female piece, wherein the ferrule is to be compressed between the male piece and the female piece when being assembled.

16. The fitting according to claim 15, wherein the male piece and the female piece have cooperating threads to be connected to one another by screwing upon assembling the male piece and the female piece.

17. A fluidic device for processing a fluidic sample, the fluidic device comprising:
  a capillary for conducting the fluidic sample;
  another component to be coupled to a first end of the capillary;
  a processing element coupled to a second end of the capillary and being configured for interacting with the fluidic sample for processing the fluidic sample; and
  the fitting according to claim 13 for coupling the capillary to the other component.

18. A method of designing the single-piece ferrule according to claim 1, the method comprising:
  configuring the lumen of the ferrule body for receiving said at least the part of the capillary;
  configuring the tapering front part of the ferrule body for forming the sealed connection with the housing of the fitting; and
  configuring the annular undercut of the back side of the tapering front part to thereby adjust frictional contact characteristics between the ferrule and the housing.

19. A method of coupling a capillary to another component of a fluidic device utilizing the fitting according to claim 13, the method comprising:
  receiving said at least the part of the capillary in the lumen of the ferrule body of the single-piece ferrule of the fitting; and
  forming the sealed connection between the tapering front part of the single-piece ferrule and the housing of the fitting, wherein the back side of the tapering front part has the annular undercut.

\* \* \* \* \*